United States Patent [19]

Cheng et al.

[11] 4,395,969

[45] Aug. 2, 1983

[54] FISH CULTURE BY SUCKER, STICKLEBACK, CARP AND BULLHEAD CATFISH ERADICATION

[75] Inventors: Fred F. Cheng, Conoga Park, Calif.; Craig MacPhee, Coeur d'Alene, Id.

[73] Assignee: College of Forestry, Wildlife & Range Sciences, University of Idaho, Moscow, Id.

[21] Appl. No.: 303,341

[22] Filed: Sep. 18, 1981

[51] Int. Cl.$^3$ .............................................. A01K 61/00
[52] U.S. Cl. .................................. 119/3; 424/DIG. 9
[58] Field of Search ...................... 119/3; 424/DIG. 9

[56] References Cited

U.S. PATENT DOCUMENTS 3,389,685 6/1968 MacPhee et al. ........................... 119/3
4,221,782 9/1980 MacPhee et al. ......................, 424/127

OTHER PUBLICATIONS

FAO Fisheries Technical Paper 100 "Reclamation of Ponds, Lakes and Streams with Fish Toxicants: A Review" by Lennon et al.
U.S. Department of the Interior July 1971 pages 49 and 51.
Lethal Effects of 1888 Chemicals upon four species of fish from Western North America by MacPhee and Ruelle, University of Idaho, Bulletin No. 3:1–112, 1969, page 79.

*Primary Examiner*—Hugh R. Chamblee
*Attorney, Agent, or Firm*—Wells, St. John & Roberts

[57] ABSTRACT

Control of stickleback, sucker, carp and bullhead catfish is accomplished by adding to their aqueous habitat a compound containing diethyl esters of phosphoric, phosphorous, thiophosphonic and thiophosphorous acid that contain a chloride or a chlorinated or vinyl group.

6 Claims, No Drawings

FISH CULTURE BY SUCKER, STICKLEBACK, CARP AND BULLHEAD CATFISH ERADICATION

BACKGROUND OF THE INVENTION

This invention relates to the improvement of fish culture through control of the sucker and stickleback by treating its aquatic habitats with diethyl esters of phosphoric, phosphorous, thiophosphoric and thiophosphorous acid that contain a chloride or a chlorinated ethyl or vinyl group.

Selective toxicants are beneficial because they eradicate pest fish without harm to natural stocks of desirable species. They alter the balance between predator and prey which enhances biological control of the pest species.

Suckers have always been abundant. Sixty-five species of suckers exist in North America. Due to the construction of reservoirs, large shallow land areas have been flooded which provide ideal sucker habitats. This has enabled the sucker to thrive and greatly increase its range in tributary streams. Because of their large size, adult suckers have an exceptionally good rate of survival and form 80 to 95 percent of the weight of fish found in some streams. Suckers greatly reduce the populations of food for game fishes with which they compete, which usually are species of salmon and trout in western North America. The results are that resident trout and salmon are scarce where sucker populations abound. Because suckers have practically no value as a sport or commercial fish, they are considered a pest fish and constitute an aggravating problem wherever they exist in competition with desirable species of fish.

Five species of the stickleback family exist in North America of which the threespine stickleback (*Gasterosteus aculeatus*) is the most notorious pest. The threespine stickleback is almost circumpolar in distribution and is normally found in marine, brackish and fresh waters of the northern hemisphere.

The stickleback has a high reproductive potential; as many as 600 eggs have been found in one nest. The fact that the male guards the nest and newly hatched young enhances juvenile survival. The stickleback has the advantage of a much shorter generation time (one to two years) than most salmon and trout (two to seven years). This permits the stickleback to increase their numbers at a faster rate than salmonids and become extremely abundant. Furthermore, stickleback have an exceptionally high rate of survival since they take advantage of inshore areas where large predators are not commonly found.

Stickleback greater reduce the populations of food and game fishes, usually species of salmon and trout, with which they compete. Furthermore, it is a successful competitor for limited food supplies and attacks juvenile salmon and trout. The result is that trout and salmon are usually scarce where stickleback populations abound. Since stickleback have no value as a sport or commercial fish, they are considered a pest fish and constitute an aggravating problem wherever they exist in conjunction with desirable species of fish.

Spot poisoning of sucker and stickleback populations with general toxicants like rotenone and toxaphene has been ineffective in controlling sucker and stickleback numbers because any benefits are very temporary and such methods are often carried out at the expense of killing natural stocks of desirable species.

Generally the sucker and stickleback are most prolific in waters containing salmonids and other cold water fishes, whereas carp and bullhead catfish are more prolific in warm waters. Manmade introductions of carp and bullheads into salmonid waters has resulted in them becoming pest fishes. In many instances, introduced carp and bullheads have thrived and competed for food and space with valuable food and sport fishes. Where carp and bullheads dominate an ecosystem, salmonids are essentially excluded. In such cases when carp and bullheads are eradicated and the waters stocked with salmon and/or trout the salmonids thrive.

Often bullhead catfish are so prolific that they become stunted and parasitized. Sometimes they prey upon more desirable fish and compete with them for food. They generally are considered a pest fish in channel catfish ponds.

Accordingly, it is an object of this invention to protect the native populations of food and game fishes by the rapid and substantial reduction of sucker, stickleback, carp and bullhead catfish populations.

It is another object of this invention to provide a simple and economic means for the destruction of sucker, stickleback, carp and bullhead catfish in the immature and adult stages.

It is a further object of this invention to provide a poison which will effect a substantially complete eradication of sucker, stickleback, carp and bullhead catfish in any waters without causing significant harm to or mortality of game and food fish or other desirable aquatic species.

It is a further object of this invention to control the sucker and stickleback population by means of diethyl esters of phosphoric, phosphorous, thiophosphate and thiophosphorous acids that contain a chloride or chlorinated ethyl or vinyl group.

It is a further object of this invention to control the carp and bullhead catfish population by means of diethyl esters of phosphoric, phosphorous, thiophosphoric and thiophosphorous acids that contain a halide or a double halogenated ethyl or vinyl group.

It is a further object of this invention, although not a necessary part of it, to use activated carbon as a deactivator for derivatives of the organophosphates mentioned above to minimize the impact of these chemical compounds on desirable fishes and other organisms in the environment and in domestic water supplies.

It is a further object of this invention, although not a necessary part of it, to use potassium permanganate as a deactivator for derivatives of the organophosphates mentioned above to minimize the impact of these chemical compounds on desirable fishes and other organisms in the environment.

DESCRIPTION OF THE PREFERRED EMBODIMENTS

Fish culture can be effectively improved through control of the sucker and stickleback by treating its aquatic habitats with diethyl esters of phosphoric, phosphorous, thiophosphoric and thiophosphorous acid that further contains a chloride or a chlorinated ethyl or vinyl group. Examples of these chemicals are as follows:

diethyl chlorophosphate

-continued diethyl chlorothiophosphite

$$C_2H_5-O\diagdown \!\!\!\!\! \diagup\!\!\!\!\!\!\!P\!\!\!\!\!\diagdown\!\!\!\!\!\diagup O$$
$$C_2H_5-O \quad\quad\quad Cl$$

diethyl chlorophosphite

Structure: $(C_2H_5O)_2P-Cl$ with S double bond diethyl chlorophosphite

Structure: $(C_2H_5O)_2P-Cl$

1,2-dichloroethyl diethyl phosphate

$(C_2H_5O)_2P(O)OCHClCH_2Cl$

2,2-dichlorovinyl diethyl phosphate

$(C_2H_5O)_2P(O)OCH=CCl_2$

O,O—diethyl S—(2,2-dichlorovinyl)thiophosphate

$(C_2H_5O)_2P(S)SCH=CCl_2$

2,2,1-trichlorovinyl diethyl phosphate

$(C_2H_5O)_2P(O)OCCl=CCl_2$ (with H)

2,2,2,1-tetrachloroethyl diethyl phosphate

$(C_2H_5O)_2P(O)OCHClCCl_3$

2,2-dichloro-1-diethyl phosphonovinyl diethyl phosphate

Structure containing two phosphate groups linked via a =CCl_2 vinyl system

We have verified that all nine of the above organophosphates are specific for the sucker and/or stickleback. As examples, we have set out in detail below the activity of 2,2-dichlorovinyl diethyl phosphate and 2,2,2,1-tetrachloroethyl diethyl phosphate with the sucker and stickleback as target fishes and salmonids as desirable fishes. In addition, we have indicated the synergistic activity of the two chemicals when they are used in combination.

This invention also relates to the improvement of fish culture through control of the carp and bullhead catfish by treating its aquatic habitats with diethyl esters of phosphoric, phosphorous, thiophosphoric and thiophosphorous acid that contain a double chlorinated ethyl or vinyl group. Examples of these chemicals from the above list are as follows:

1,2-dichloroethyl diethyl phosphate $(C_2H_5O)_2P(O)OCHClCH_2Cl$ 2,2-dichlorovinyl diethyl phosphate $(C_2H_5O)_2P(O)OCHCCl_2$ O,O-diethyl S-2(2,2-dichlorovinyl)thiophosphate $(C_2H_5O)_2P(S)SCHCCl_2$ We have verified that 2,2-dichlorovinyl diethyl phosphate is specific for the carp and bullhead catfish.

Two of the nine listed toxicants were discovered in bioassays that tested a series of different highly toxic chemicals, one at a time, for selectively. The bioassays exposed target and desirable fishes simultaneously in the same aquarium to a potential chemical candidate.

The selectivity of the two toxicants to suckers and stickleback was discovered by systematically screening about 1000 chemicals with suckers and 1700 chemicals with stickleback that were known to be highly toxic to fishes. Two target fish, and two salmonids were exposed together to low concentrations of single toxicants in 24-hour bioassays at about 15 degrees Celsius. The order and time of death of each species of fish were noted. The results of this procedure indicated that 1,2-dichloroethyl diethyl phosphate and O,O-diethyl S-(2,2-dichlorovinyl)thiophosphate were extremely selective for suckers and stickleback and harmless to salmonids.

Derivatives of the two initially discovered chemicals were then screened for selective properties. Of these only the diethyl esters of phosphoric and phosphorothioic acids that contained chlorine or a chlorinated ethyl or vinyl group were selective for the suckers and stickleback. Other derivations were not.

The selectivity of 2,2-dichlorovinyl diethyl phosphate to carp and bullhead catfish was discovered after the selectivity of the chemical to the sucker and stickleback was found.

Bioassay Procedures

Bioassays utilized water from an artesian well at Moscow, Idaho and from the headwaters of the Palouse River, also in Idaho. The chemical characteristics of the artesian water were analyzed as follows: Total hardness 67–120 mg/l; total dissolved solids, 160–175 mg/l; and pH 7.1. The chemistry of the Palouse River water was analyzed as follows: total hardness 17 mg/l; methyl orange alkalinity 26 mg/l; total dissolved solids, 32 mg/l and pH, 7.0.

The desirable fishes delineated in bioassays included coho salmon (*Oncorhynchus kisutch*), sockeye salmon (*O. nerka*), kokanee (a land-locked subspecies of sockeye salmon), chinook salmon (*O. tschawytscha*), steelhead, a sea-run variety of the rainbow trout (*Salmo gairdneri*), Kamloops (an adfluvial rainbow trout), the cutthroat trout (*S. clarki*), and brook trout (*Salvelinus fontinalis*).

The target fishes delineated in bioassays included bridgelip sucker (*Catastomus columbianus*), white sucker (*C. commmersoni*), threespine stickleback (*Gasterosteus aculeatus*), brook stickleback (*Eucalia incon-* stans), brown bullhead (*Ictalurus nebulosus*), the carp (*Cyprinus carpio*).

Cursory bioassays were made with small numbers of other fishes and a crayfish (*Pacifasticus klamathensis*) to check on the universal selectivity of the toxicants. The fishes included Arctic grayling (*Thymallus arcticus*), longnose sucker (*C. catastomus*), largescale sucker, (*C. macrocheilus*), and spotted sucker (*Minytrema melanops*).

Fish were acclimated to test temperatures, usually at 5, 7.5, 10, 15 and 20 degrees Celsius (C), at least 60 hours before exposure to toxicants. For fish and crayfish four water baths regulated the temperature of assay aquaria. Each water bath contained a battery of 20 identical 19-liter clear glass containers or 11.4-liter plastic aquaria lined with disposable polyethylene bags and covered with Plexiglass lids to reduce evaporation. For larger fish and large numbers of fish the bioassays were made in two temperature controlled rooms that contained a series of 700-liter circular fiberglass vats and a series of 76- and 91-liter plastic containers.

Comparative tests with dichloro- and tetrachloro-compounds in plastic containers, polyethylene bags and glass jars gave uniform results. No difference in results were noted that could be attributed to the use of fiberglass vats.

Standard bioassay techniques were used in sorting fish and conducting the tests. Fish were placed in aerated test aquaria overnight to permit fish to recover from stress due to handling and to deprive them of food. The average load varied but most bioassays were conducted with about 1 g of fish per liter of water.

Aliquots of organophosphates were dissolved in ethanol and dispensed to the aquaria to provide concentrations suitable for obtaining the $LC_0$ and $LC_{50}$ of desirable fish and the $LC_{50}$ and $LC_{100}$ of target fish. Control fish were conditioned in the same manner as the test fish, but no chemical was added to the control vessels during the assays. The control datum is the first concentration (0.0) reported in the table. After the addition of a chemical, observations were made mainly at 3, 6, 12, 24, 48, 96, and 192 h. The weight and fork length of fish were obtained when fishes were sacrificed. The fork length ranges of test fish are given in tables of the examples.

Attention was directed to the lethal concentrations of toxicant resulting in 50% mortality of pest fish ($LC_{50}$) and that resulting in 100% mortality ($LC_{100}$). Similarly, tests were conducted to identify lethal concentrations of toxicant resulting in no mortality to desirable species ($LC_0$) and that resulting in 50% mortality ($LC_{50}$).

Delineation bioassays determined primarily the $LC_{50}$ and $LC_{100}$ of sucker and stickleback and the $LC_0$ and $LC_{50}$ of salmonids. The selectivity index $LC_{50}/LC_{50}$ compares the lethal concentrations that cause 50% mortalities for each species. The safety index $LC_0/LC_{100}$ compares the maximum concentration that kills 0% of a preferred species with the minimum concentration that kills 100% of a target species.

The statistical $LC_1$, $LC_{50}$, and $LC_{99}$ were interpolated and/or extrapolated using probit graph paper to approximate the $LC_0$, $LC_{50}$, and $LC_{100}$ when the latter set of values was not closely determined by single concentrations in a series.

Additive indices were calculated for assessment of toxicity or efficacy of mixtures of chemicals in fish bioassays (Marking and Dawson 1975). The toxicities ($LC_{50}$,s) of two individual chemicals ($A_i$ and $B_i$) and mixtures of the two chemicals ($A_m$ and $B_m$) are summed according to the formula:

$$\frac{A_m}{A_i} + \frac{B_m}{B_i} = S$$

where S is the sum of the biological activity. To achieve linearity a formula $$\frac{(1)}{S} - 1$$

is used to calculate the additive index where the value of S is equal to or less than 1.0. (For values of S equal to or more than one the formula $S(-1)+1$ may be used to calculate the additive index.) Additive indices equal to zero represent additive toxicity; values greater than zero represent synergistic activity; and values less than zero weaken or neutralize biological activity.

EXAMPLE 1

(Temperature delineation of 2,2-dichlorovinyl diethyl phosphate.)

Threespine stickleback, brook stickleback, bridgelip sucker, white sucker, chinook salmon, sockeye salmon, steelhead trout, Kamloops trout, cutthroat trout, and brook trout were treated with various concentrations of 2,2-dichlorovinyl diethyl phosphate and at various temperatures to determine approximate selectivity and safety indices. The approximate $LC_{50}$ and $LC_{100}$ of the target fishes (threespine and brook sticklebacks and bridgelip and white suckers) are tabulated in Table 1. The approximate $LC_0$ and $LC_{50}$ of the desirable fishes (the salmons and trouts) are tabulated in Table 2. The 96-hour selectivity and safety indices of selected species of salmonids versus the three-spine stickleback are tabulated in Table 3. The 96-hour selectivity and safety indices of selected species of salmonids versus the bridgelip sucker are tabulated in Table 4.

TABLE 1

| Species | Lethal Concentration mg/l | Temperature C. | Elapsed time, hours | | | |
|---|---|---|---|---|---|---|
| | | | 24 | 48 | 96 | 192 |
| Threespine stickleback | $LC_{50}$ | 5 | — | 2.3 | 1.0 | 0.8 |
| | | 10 | 1.5 | 0.8 | 0.6 | 0.5 |
| | | 15 | 0.8 | 0.7 | 0.6 | 0.6 |
| | | 20 | 0.5 | 0.4 | — | — |
| | $LC_{100}$ | 5 | — | >3.0 | 3.0 | 1.0 |
| | | 10 | >3.0 | 1.5 | 1.0 | 0.6 |
| | | 15 | 2.0 | 2.0 | 1.0 | 1.0 |
| | | 20 | 1.0 | 0.6 | 0.6 | 0.6 |
| Brook stickleback | $LC_{50}$ | 15 | 0.8 | 0.4 | 0.4 | 0.3 |
| | $LC_{100}$ | 15 | 1.0 | 0.6 | 0.6 | 0.6 |
| Bridgelip sucker | $LC_{50}$ | 5 | — | 0.22 | 0.15 | 0.10 |
| | | 10 | 0.23 | 0.12 | 0.08 | 0.06 |
| | | 15 | 0.18 | 0.07 | 0.05 | 0.05 |
| | | 20 | 0.08 | 0.05 | 0.04 | 0.03 |
| | $LC_{100}$ | 5 | — | 0.30 | 0.30 | 0.15 |
| | | 10 | 0.50 | 0.30 | 0.10 | 0.10 |
| | | 15 | 0.30 | 0.10 | 0.10 | 0.10 |
| | | 20 | 0.10 | 0.07 | 0.07 | 0.07 |
| White sucker | $LC_{50}$ | 20 | 0.10 | 0.07 | 0.06 | 0.05 |
| | $LC_{100}$ | 20 | — | — | 0.10 | 0.10 |

TABLE 2

| Species | Lethal Concentration mg/l | Temperature, C. | Elapsed time, hours | | |
|---|---|---|---|---|---|
| | | | 48 | 96 | 192 |
| Chinook | $LC_0$ | 10 | 8.0 | 6.0 | 4.0 |

TABLE 2-continued

| Species | Lethal Concentration mg/l | Temperature, C. | Elapsed time, hours 48 | 96 | 192 |
|---|---|---|---|---|---|
| salmon | | 15 | | 3.0 | 2.7 | — |
| | $LC_{50}$ | 10 | 10.4 | 7.0 | 5.0 |
| | | 15 | 4.0 | 3.4 | — |
| Sockeye salmon | $LC_0$ | 7.5 | >10.0 | 6.0 | 2.0 |
| | | 10 | 6.0 | 3.0 | 2.0 |
| | $LC_{50}$ | 7.5 | >10.0 | 9.0 | 4.0 |
| | | 10 | >8.0 | 6.0 | 3.4 |
| Steelhead trout | $LC_0$ | 5 | 6.0 | 4.0 | 1.5 |
| | $LC_{50}$ | 5 | — | 7.1 | 2.8 |
| Kamloops trout | $LC_0$ | 5 | >4.0 | 2.0 | 1.4 |
| | | 10 | >4.0 | 2.0 | 1.0 |
| | | 15 | 3.0 | 1.0 | 1.0 |
| | $LC_{50}$ | 5 | — | — | 5.1 |
| | | 10 | — | 5.4 | 2.0 |
| | | 15 | — | 3.5 | 3.0 |
| Cutthroat trout | $LC_0$ | 10 | — | 4.0 | — |
| | | 15 | 4.0 | 2.0 | 1.0 |
| | $LC_{50}$ | 10 | — | — | 4.8 |
| | | 15 | 5.3 | 2.5 | 1.8 |
| Brook trout | $LC_0$ | 15 | 4.0 | 2.0 | 0.8 |
| | $LC_{50}$ | | 5.0 | 3.3 | 3.2 |

TABLE 3

| Species | Temperature, C. | Selectivity index | Safety index |
|---|---|---|---|
| Chinook | 10 | 11.7 | 6.0 |
| | 15 | 5.7 | 2.7 |
| Sockeye | 7.5 | 10.2 | 3.0 |
| | 10 | >10.0 | 3.0 |
| Steelhead | 5 | 7.1 | 1.3 |
| Kamloops | 5 | | 0.7 |
| | 10 | 9.0 | 2.0 |
| | 15 | 5.7 | 1.0 |
| Cutthroat | 10 | >8.0 | 4.0 |
| | 15 | 4.2 | 2.0 |
| Brook | 15 | 5.5 | 2.0 |

TABLE 4

| Species | Temperature, C. | Selectivity index | Safety index |
|---|---|---|---|
| Chinook | 10 | 87 | 60 |
| | 15 | 68 | 27 |
| Sockeye | 7.5 | 100 | 30 |
| | 10 | 75 | 30 |
| Steelhead | 5 | 47 | 13 |
| Kamloops | 5 | >34 | 7 |
| | 10 | 67 | 20 |
| | 15 | 70 | 10 |
| Cutthroat | 10 | >60 | 40 |
| | 15 | 50 | 20 |
| Brook | 15 | 66 | 20 |

Table 1 shows that 50% mortality ($LC_{50}$) and 100% mortality ($LC_{100}$) concentrations of stickleback and sucker are inversely correlated with temperature and with the duration of the bioassays. In addition, Table 1 shows that 2, 2-dichlorovinyl diethyl phosphate was about 10 times more potent for suckers than for stickleback.

Table 2 shows that 0% mortality ($LC_0$) and 50% mortality ($LC_{50}$) concentrations of salmonids are inversely correlated with temperature and the duration of the bioassays.

Table 3 shows that in 96-hour assays for salmonids versus the threespine stickleback the selectivity indices ranged from 8 to 11.7 at 10 C. and from 4.2 to 5.7 at 15 C. and the safety indices ranged from 2 to 6 at 10 C. and from 1 to 2.7 at 15 C.

Table 4 shows that in, 96-hour assays for salmonids versus the bridgelip sucker the selectivity indices ranged from 60 to 87 at 10 C. and from 50 to 70 at 15 C. and the safety indices ranged from 20 to 60 at 10 C. and from 10 to 27 at 15 C.

EXAMPLE 2

(Temperature delineations of 2, 2, 2, 1-tetrachloroethyl diethyl phosphate)

Threespine stickleback, brook stickleback, bridgelip sucker, white sucker, chinook salmon, coho salmon, sockeye salmon, kokanee, Kamloops trout, cutthroat trout, and brook trout were treated with various concentrations of 2, 2, 2, 1-tetrachloroethyl diethyl phosphate and at various temperatures to determine approximate selectivity and safety indices. The approximate $LC_{50}$ and $LC_{100}$ of the target fishes (threespine and brook sticklebacks and bridgelip and white suckers) are tabulated in Table 5. The approximate $LC_0$ and $LC_{50}$ of the desirable fishes (the salmons and trouts) are tabulated in Table 6. The 96-hour selectivity and safety indices of selected species of salmonids versus the threespine stickleback are tabulated in Table 7. The 96-hour selectivity and safety indices of selected species of salmonids versus the bridgelip sucker are tabulated in Table 8.

TABLE 5

| Species | Lethal concentration μg/l | Temperature, C. | Elapsed time, hours 24 | 48 | 96 | 192 |
|---|---|---|---|---|---|---|
| Threespine stickleback | $LC_{50}$ | 5 | | 8 | <7 | <7 |
| | | 10 | 8.5 | 4 | 4 | 4 |
| | | 15 | 7 | 4 | 4 | 4 |
| | | 20 | 3 | <3 | <3 | <3 |
| | $LC_{100}$ | 5 | 23 | 13 | 10 | 10 |
| | | 10 | 16 | 10 | 7–10 | 10 |
| | | 15 | 13 | 7 | 7 | 7 |
| | | 20 | 5 | 5 | 5 | 5 |
| Brook stickleback | $LC_{50}$ | 15 | 6 | | | |
| | $LC_{100}$ | 15 | 10 | 8 | 6 | |
| Bridgelip sucker | $LC_{50}$ | 7.5 | 12 | 7 | 5 | |
| | | 15 | 5–8 | 3 | 2.5 | |
| | $LC_{100}$ | 7.5 | 20 | 11 | 7 | |
| | | 15 | 10 | 9 | 5–7 | |
| White sucker | $LC_{50}$ | 15 | 4 | <3 | | |
| | $LC_{100}$ | 15 | 10 | 10 | | |

TABLE 6

| Species | Lethal concentration μg/l | Temperature, C. | Elapsed time, hours 48 | 96 | 192 |
|---|---|---|---|---|---|
| Chinook Salmon | $LC_0$ | 10 | 30 | 20 | 18 |
| | $LC_{50}$ | | 35 | 25 | 25 |
| Coho salmon | $LC_0$ | 10 | 30 | 14 | 8 |
| | $LC_{50}$ | | | 23 | 15 |
| Sockeye salmon | $LC_0$ | 7.5 | 36 | 14 | 10 |
| | | 10 | 20 | 12 | 10 |
| | $LC_{50}$ | 7.5 | 50 | 20 | 14 |
| | | 10 | 30 | 17 | 16 |
| Kokanee | $LC_0$ | 15 | 30 | 20 | 20 |
| | $LC_{50}$ | | 40 | 30 | 27 |
| Kamloops trout | $LC_0$ | 5 | | 24 | 12 |
| | | 10 | | 18 | 10 |
| | | 15 | | 24 | 14 |
| | $LC_{50}$ | 5 | >30 | 18 | |
| | | 10 | | 24 | 20 |
| | | 15 | | >24 | >24 |
| Cutthroat trout | $LC_0$ | 10 | | 14 | 14 |
| | | 15 | 14 | 14 | 14 |
| | $LC_{50}$ | 10 | | 19 | 17 |
| | | 15 | 22 | 18 | 18 |
| Brook | $LC_0$ | 15 | 10 | 10 | 10 |

TABLE 6-continued

| Species | Lethal concentration μg/l | Temperature, C. | Elapsed time, hours 48 | 96 | 192 |
|---|---|---|---|---|---|
| trout | $LC_{50}$ | | 22 | 20 | 20 |

TABLE 7

| Species | Temperature, C. | Selectivity index | Safety index |
|---|---|---|---|
| Chinook | 10 | 5.0 | 2.9 |
| Coho | 10 | 4.3 | 2.0 |
| Sockeye | 7.5 | 4.0 | 2.0 |
| Kokanee | 15 | 12.0 | 3.3 |
| Kamloops | 5 | 6.0 | 3.4 |
| | 10 | 6.8 | 2.6 |
| | 15 | 9.8 | 4.0 |
| Cutthroat | 10 | 3.8 | 2.0 |
| | 15 | 7.2 | 2.3 |
| Brook | 15 | 8.0 | 1.7 |

TABLE 8

| Species | Temperature, C. | Selectivity index | Safety index |
|---|---|---|---|
| Chinook | 10 | 6.3 | 2.4 |
| Coho | 10 | 5.8 | 1.7 |
| Sockeye | 10 | 7.5 | 1.4 |
| Kokanee | 15 | 7.5 | 2.9 |
| Kamloops | 5 | 4.3 | 2.4 |
| | 10 | 6.0 | 1.8 |
| | 15 | 6.0 | 2.1 |
| Cutthroat | 10 | 4.8 | 1.7 |
| | 15 | 4.5 | 2.0 |
| Brook | 15 | 5.0 | 1.4 |

The effect of water quality on the potency of 2, 2, 2,-1 tetrachloroethyl diethyl phosphate to threespine stickleback was demonstrated by simultaneously assaying fish in river water containing relatively small amounts of total dissolved solids (32 mg/l) and in artesian well water which contains relatively large amounts of total dissolved solids (160–175 mg/l). The results of the bioassays showed that in either artesian well or river water in a 96-hour bioassay a 100% mortality of threespine stickleback was achieved at a concentration of 7 mg/l at 10 C. The chemistry of the water made no difference to the potency of the chemical.

Table 5 shows that 50% mortality ($LC_{50}$) and 100% mortality ($LC_{100}$) concentrations of stickleback and suckers are inversely correlated with temperature and with the duration of bioassays. In addition, Table 5 shows that 2, 2, 2, 1-tetrachloroethyl diethyl phosphate was about equally potent to sucker and stickleback.

Table 6 shows that 0% mortality ($LC_0$) and 50% mortality ($LC_{50}$) concentrations of salmonids are inversely correlated with temperature and the duration of the bioassays.

Table 7 shows that in 96-hour assays for salmonids versus threespine stickleback the selectivity indices ranged from 4.8 to 7.5 at 10 C. and from 4.5 to 7.5 at 15 C. and that the safety indices ranged from 1.4 to 2.4 at 10 C. and 1.4 to 2.9 at 15 C.

Table 8 shows that in 96-hour assays for salmonids versus bridgelip sucker the selectivity indices ranged from 3.8 to 6.8 at 10 C. and from 7.2 to 12.0 at 15 C. and the safety indices ranged from 2.0 to 2.9 at 10 C. and from 1.7 to 4.0 at 15 C.

EXAMPLE 3

(Exploratory synergistic tests.)

Threespine stickleback and chinook salmon were treated with 2, 2-dichlorovinyl diethyl phosphate and 2, 2, 2, 1-tetrachloroethyl diethyl phosphate in combination. Stickleback and chinook were treated with a series of selected ratios of the above two phosphates at 10 C. to determine ratios that were both effective and economically practical for controlling stickleback but harmless to salmonids.

In a 96-hour assay in artesian well water at 10 C. a 100% mortality of threespine stickleback was achieved with a mixture of concentrations as small as 600 μg/l of 2, 2-dichlorovinyl diethyl phosphate and 2.0 μg/l of 2, 2, 2, 1-tetrachloroethyl diethyl phosphate.

The addition of a small amount of the tetrachloro-compound (2 μg/l) lowered the minimum effective amount ($LC_{100}$ of stickleback) of the less potent dichloro-chemical from 1000 μg/l to 600 μg/l. The data resulting from the combinations tested suggest that as little as 1 part of the tetrachloro- to 300 parts of the dichloro-compound is effective and the most practical to use economically. For these reasons a 300:1 combination was used in the following examples for additive and synergistic effects.

In 96-hour assays in artesian well water at 10 C. no mortality of chinook occurred at a concentration of 2500 μg/l of 2, 2-dichlorovinyl diethyl phosphate in combination with a concentration of 2.5 μg/l of 2, 2, 2, 1-tetrachloroethyl diethyl phosphate.

Synergistic bioassays with suckers were limited to one test containing two bridgelip suckers (both 55 mm). They were exposed to concentrations of 60 μg/l of 2, 2-dichlorovinyl diethyl phosphate and 0.2 μg/l of 2, 2, 2, 1-tetrachloroethyl diethyl phosphate in combination in 10 l of artesian well water (load, 0.4 g/l) at 10 C. The combination of chemicals killed the suckers in 72 hours. In contrast the 96-hour $LC_{100}$ of the bridge-lip sucker exposed to 2, 2-dichlorovinyl diethyl phosphate only is 100 μg/l at 10 C., a much larger amount.

EXAMPLE 4

(Synergistic delineations.)

Threespine stickleback, sockeye salmon and Kamloops trout were separately treated with selected concentrations of 2, 2-dichlorovinyl diethyl phosphate and 2, 2, 2, 1-tetrachloroethyl diethyl phosphate applied individually and in a 300:1 combination mostly at 10 C.

In 96-hour assays in artesian well water at 10 C., 100% mortality of threespine stickleback was achieved at concentrations of 1500 μg/l of 2, 2-dichlorovinyl diethyl phosphate and 6 μg/l of 2, 2, 2, 1-tetrachloroethyl diethyl phosphate when the chemicals were tested individually and at concentrations of 300 μg/l of the dichloro-compound and 1.0 μg/l of the tetrachloro-compound when the chemicals were tested in combination.

In 96-hour assays in artesian well water at 10 C., no mortality of sockeye salmon occurred at concentrations of 3000 μg/l of 2, 2-dichlorovinyl diethyl phosphate and 10 μg/l of 2, 2, 2, 1-tetrachloroethyl diethyl phosphate when the chemicals were tested individually and at concentrations of 2100 μg/l of the dichloro- and 7 μg/l of the tetrachloro-compound when the two chemicals were used in combination.

In 96-hour assays in artesian well water at 10 C., no mortality of Kamloops trout occurred at concentrations of 2000 μg/l of 2, 2-dichlorovinyl diethyl phosphate and 14 μg/l of 2, 2, 2, 1-tetrachloroethyl diethyl phosphate when the chemicals were tested individually and at concentrations of 1800 μg/l of the dichloro-compound and 6 mg/l of the tetrachloro-compound when the chemicals were tested in combination.

Table 9 shows that in 96-hour assays at 10 C. for sockeye salmon versus threespine stickleback and for Kamloops trout versus the threespine stickleback the selectivity and safety indices are larger for a 300 to 1 ratio of the dichloro- and tetrachloro-compounds when the chemicals were tested in combination than when compounds were tested individually (See Tables 4 and 8).

TABLE 9

| Organo-phos-phate | Species | $LC_{50}$ μg/l | Selectivity index | $LC_0$ μg/l | $LC_{100}$ μg/l | Safety index |
|---|---|---|---|---|---|---|
| 2 Cl | Sockeye | 6000 | 6.0 | 3600 | | 3.0 |
| | Stickleback | 1000 | | | 1200 | |
| 4 Cl | Sockeye | 17 | 4.2 | 12 | | 2.0 |
| | Stickleback | 4 | | | 6 | |
| 2 Cl & 4 Cl in combination | Sockeye | 2400 & 8 | 8.0 | 2100 & 7 | | 3.5 |
| | Stickleback | 300 & 1 | | | 600 & 2 | |
| 2 Cl | Kamloops | 5000 | 5.0 | 2000 | | 1.7 |
| | Stickleback | 1000 | | | 1200 | |
| 4 Cl | Kamloops | 24 | 6.0 | 14 | | 2.3 |
| | Stickleback | 4 | | | 6 | |
| 2 Cl & 4 Cl in combination | Kamloops | 2400 & 8 | 8.0 | 1800 & 6 | | 3.0 |
| | Stickleback | 300 & 1 | | | 600 & 2 | |

EXAMPLE 5

(Additive indices)

Additive indices for stickleback, sockeye and Kamloops trout were calculated to assess the toxicity or efficacy of mixtures of 2, 2-dichlorovinyl diethyl phosphate and 2, 2, 2, 1-tetrachloroethyl diethyl phosphate at 10 C. The values of the indices are tabulated in Table 10.

TABLE 10

| Species | Elapsed time, hours | Organo-phosphate | $LC_{50}$ μg/l Individually | $LC_{50}$ μg/l In combination | Additive index |
|---|---|---|---|---|---|
| Stickleback | 96 | 2 Cl | 1000 | 300 | 0.82 |
| | | 4 Cl | 4 | 1.0 | |
| | 192 | 2 Cl | 800 | 200 | 1.13 |
| | | 4 Cl | 3 | 0.67 | |
| Sockeye | 96 | 2 Cl | 6000 | 2400 | 0.15 |
| | | 4 Cl | 17 | 8 | |
| | 192 | 2 Cl | 3600 | 1800 | 0.11 |
| | | 4 Cl | 15 | 6 | |
| Kamloops | 96 | 2 Cl | 5000 | 2400 | 0.23 |
| | | 4 Cl | 24 | 8 | |
| | 192 | 2 Cl | 2000 | 1500 | 0.00 |
| | | 4 Cl | 20 | 5 | |

In 96-hour assays at 10 C. with the dichloro- and tetrachloro-compounds applied individually and in combination to salmonids and stickleback, the additive index was 0.82 for threespine stickleback, 0.15 for sockeye and 0.23 for Kamloops. This indicates that the two chemicals in combination are more synergistic for stickleback than for salmonids.

EXAMPLE 6

(Long-term static bioassays)

Threespine stickleback and chinook and coho salmon were treated with 2, 2-dichlorovinyl diethyl phosphate and 2, 2, 2, 1-tetrachloroethyl diethyl phosphate applied individually and in a 300:1 combination in 64-day bioassays in 500 l of river water at 10 C.

Each aquarium contained a 5 cm deep layer of 2 cm diameter granitic gravel on the 6000 $cm^2$ bottom. A thin layer of river mud was added to simulate a natural ecosystem. A solution of 100 ml of mud was stirred into each aquarium and allowed to settle on top of the gravel one week prior to the start of the assays. The mud seeded the aquarium water with bacteria and other lower organisms in order to help process the waste metabolites of fishes and degrade the organophosphates.

A first series of assays tested stickleback and coho together; a second series of assays tested stickleback and chinook together. Fish were fed a diet of 3% of their body weight per day of a commercial hatchery diet for the first 14 days and 2% of their body weight per day thereafter. One crayfish (about 1.6 g) was added to each aquarium in the second series. The water in each aquarium was aerated with a single stone air breaker but the water was not filtered.

In a 32-day observation period at 10 C., 65% mortality of the threespine stickleback was achieved at concentrations of 600 μg/l of 2, 2-dichlorovinyl diethyl phosphate and 100% mortality of the three-spine stickleback at concentrations of 4 μg/l of 2, 2, 2, 1-tetrachloroethyl diethyl phosphate when the chemicals were tested individually. Essentially no mortality occurred at concentrations of 300 μg/l of the dichloro-compound and 1 μg/l of the tetrachloro-compound when the two chemicals were used in combination.

In a 64-day assay in river water at 10 C., no significant mortality (as compared with controls of chinook or coho salmon) occurred at concentrations of 300 μg/l of 2, 2-dichlorovinyl diethyl phosphate nor at 6 μg/l of 2, 2, 2, 1-tetrachloroethyl diethyl phosphate when the chemicals were tested individually, nor at concentrations of 300 μg/l of the dichloro-compound and 1 μg/l of the tetrachloro-compound when the two chemicals were used in combination.

Of the 9 crayfish tested in the second series of assays 6 were alive and 3 were missing (one crayfish in the control, one tested at 2 μg/l of the tetrachloro-compound and one tested at 200 μg/l of the dichloro- and 0.67 μg/l of the tetrachloro-compound in combination).

EXAMPLE 7

(Deactivation with activated carbon and potassium permanganate)

The inhibitory effect of activated carbon on the activity of 2, 2-dichlorovinyl diethyl phosphate was demonstrated in 192-hour assays with stickleback in river water at 15 C. The chemicals were assigned to five aquaria at concentrations indicated in Table 11. A second lot of 5 fish was added to each aquarium 18 hours after the first lot of 10 fish had died or lost their equilibrium. As the life of the first lot of fish was short, the test water was only slightly conditioned by the dying fish and any error introduced by this procedure was relatively small.

TABLE 11

| Activated carbon, mg/l | Mean survival time, hours | |
|---|---|---|
| | Bioassay started when chemical was added (10 fish per concentration) | Bioassay started 18 hours after chemical was added (5 fish per concentration) |
| 0 | 7.5 | 9.5 |
| 4 | 9.2 | 8.0 |
| 8 | 10.8 | 33.5 |
| 16 | 12.0 | — |
| 32 | 22.0 | 95.0[a] |

[a] 1 fish did not die (observed 11 days)

Table 11 indicates that activated carbon delayed mortality in stickleback that were exposed to 2 mg/l of 2, 2-dichlorovinyl diethyl phosphate. The mean survival times of stickleback were dependent on the amounts of activated carbon that were added. The table shows also that deactivation of the dichloro-compound is not instantaneous or complete. Thrity-two mg/l of carbon did not prevent the death of stickleback. On the other hand, an 18-hour deactivation period about tripled the survival time of strickleback that were used in the 8 and 32 mg/l of carbon tests.

The inhibitory effect of potassium permanganate on the activity of 2, 2-dichlorovinyl diethyl phosphate was demonstrated in 192-hour assays with chinook salmon in river water at 15 C. The chemicals were assigned to five aquaria at concentrations indicated in Table 12.

TABLE 12

| 2 Cl mg/l | $KM_nO_4$ mg/l | Equivalent weight | Elapsed time, hours | | | | |
|---|---|---|---|---|---|---|---|
| | | | 12 | 24 | 48 | 96 | 192 |
| 4 | 0.00 | 0.0 | 0 | 0 | 0 | 100(81) | |
| 4 | 0.84 | 0.5 | 0 | 0 | 0 | 100(78) | |
| 4 | 1.69 | 1.0 | 0 | 0 | 0 | 67(83) | 93(84) |
| 4 | 3.38 | 2.0 | 13 | 13 | 13 | 13(8) | 40(107) |
| 4 | 6.76 | 4.0 | 0 | 13 | 13 | 13(17) | 13(17) |

Table 12 shows that potassium permanganate delayed mortality in chinook salmon that were exposed to excessive concentrations of 2, 2-dichlorovinyl diethyl phosphate. The addition of the permanganate extended the survival time of chinook significantly. The control data with no permanganate added correspond exactly with that previously developed for the 4 mg/l concentration of the dichloro-compound at 15 C. The data for the 1 equivalent weight of permanganate added correspond closely to that previously obtained by use of a 3 mg/l concentration without permanganate. This indicates that the addition of 1 equivalent weight of permanganate deactivates 2, 2-dichlorovinyl diethyl phosphate about 25%. Higher concentrations of permanganate further deactivate the dichloro-compound.

EXAMPLE 8

(Largescale, longnose and spotted sucker)

Exploratory tests were made with other species of sucker to demonstrate that the chloride derivations of diethyl phosphate are generally selective for members of the sucker family (Catastomidae). We noted that the largescale sucker had essentially the same tolerance to the chlorinated diethyl phosphates as did the bridgelip and white suckers.

A series of 24-hour bioassays was made with the longnose sucker (1 fish per aquarium) at a concentration range of 0.1 mg/l to 4.5 mg/l of 2, 2-dichlorovinyl diethyl phosphate. The chemical killed the longnose sucker (47 to 61 mm) at a concentration of 0.2 mg/l and higher in less than 24 hours at 15 C.

A series of five 24-hour biassays was made with the spotted sucker (2 fish per aquarium) at a concentration range of 1 mg/l to 5 mg/l of 2, 2-dichlorovinyl diethyl phosphate. The chemical killed all of the spotted suckers (31 to 38 mm) at 1 mg/l in less than 24 hours at 15 C.

Three longnose suckers (about 125 mm) and three Arctic grayling (about 125 mm) were exposed to 10 μg/l of 2, 2, 2, 1-tetrachloroethyl diethyl phosphate. The suckers died between 14 and 22 hours at 13 C. The grayling were not affected in 48-hour biassays.

EXAMPLE 9

(Carp and bullhead catfish)

The selectivity of 2, 2-dichlorovinyl diethyl phosphate to carp was first discovered in an exploratory test in which the carp died first when both a small carp and salmon were placed together in an aquarium and exposed to the chemical. In a later bioassay a concentration of 1 mg/l of 2, 2-dichlorovinyl diethyl phosphate killed a 20 g carp (68 mm) in 10 l of artesian well water (load, 2.0 g/l) at 10 C. in 30 hours.

A subsequent series of bioassays tested concentrations of 0.0, 0.6, 0.8, 1.0, 1.5 and 2.0 mg/l of 2, 2-dichlorovinyl diethyl phosphate with larger carp (fork length range, 115–150 mm; mean weight, 44 g) using 10 fish per concentration (load, 0.7 g/l) and artesian well water at 10 C. A concentration of 2.0 mg/l of the chemical killed 100 percent of the carp in 24 hours and a concentration of 1.5 mg/l killed 90 percent of them in 96 hours and 100 percent in 72 hours. No fish died in the control or at a concentration of 0.6 mg/l in 192-hour bioassays. In contrast the $LC_0$ of salmonids exposed to 2, 2-dichlorovinyl diethyl phosphate varies between 4 and 8 mg/l in 48-hour bioassays and 2 and 6 mg/l in 96-hour bioassays at 10 C. (Table 2).

Bioassays (10 fish per concentration) were made with brown bullhead catfish fry (28–40 mm) at concentrations of 0, 2, and 4 mg/l of 2, 2-dichlorovinyl diethyl phosphate in artesian well water (load, 0.5 g/l). All the Bullhead catfish died in 12 hours at 2 mg/l and in 6 hours at 4 mg/l of the chemical at 10 C. The dichloro-compound is slightly more selective to bullhead than to stickleback, as the 24-hour $LC_{100}$ of the stickleback is 4 mg/l at 10 C.

A second series of bioassays (10 fish per concentration) was made with larger bullhead catfish (140–185 mm) at 0.6 and 1.0 mg/l concentrations of 2, 2-dichlorovinyl diethyl phosphate in artesian well water (load, 1.0 g/l) at 10 C. In 96 hours 50% mortality occurred at 0.6 mg/l and 100% mortality at 1.0 mg/l. The 96-hour $LC_{100}$ of stickleback is 1.0 mg/l of the dichloro-compound at 10 C.

EXAMPLE 10

(Crayfish)

A series of bioassays tested crayfish (9 to 10 crayfish per aquarium) at concentrations of 1, 3, and 10 mg/l of 2, 2-dichlorovinyl diethyl phosphate. No crayfish died at 1 mg/l and only 1 out of 9 crayfish died at 3 mg/l of the chemical in 96 hours at 10 C. No crayfish died at 10 mg/l of chemical in 24 hours at 10 C. A second series of bioassays tested crayfish (10 crayfish per aquarium) at 10 concentrations of 2, 2, 2, 1-tetrachloroethyl diethyl phosphate (range, 0 to 1400 μg/l). No crayfish died in 96 hours at concentrations of 200 μg/l or less at 10 C. These tests demonstrated that the halogenated diethyl phosphates are not generally harmful to crayfish when used at concentrations selective for stickleback, sucker, carp and bullhead catfish.

EXAMPLE 11

(Diethyl chlorophosphate, diethyl chlorothiophosphite and diethyl chlorophosphite).

A series of eight 24-hour bioassays was made with 2 three-spine stickleback and 2 steelhead placed together in the same aquarium at 15 C. The fish were exposed to concentrations of 2, 3, 4, 5, 7, 10 and 20 mg/l of diethyl chlorophosphate. The chemical killed 100% of the stickleback at 3 mg/l or more and no steelhead at 7 mg/l or less which values give a safety index of about 2.3. The $LC_{50}$'s of the chemical were 2 mg/l for the stickleback and 10 mg/l for the steelhead which values result in a selectivity index of 5.

A bioassay was made with 10 threespine stickleback, 10 largescale suckers and 10 chinook placed together in the same aquarium in artesian well water at 10 C. A concentration of 50 mg/l of diethyl chlorothiophosphite killed 100% of the sticklebacks and suckers and 0% of the chinook in 12 hours.

A bioassay was made with 2 bridgelip sucker and 2 chinook salmon placed together in the same aquarium at 10 C. A concentration of 50 mg/l of diethyl chlorophosphite killed the suckers in 4 hours and did not kill the chinook in 24 hours.

These bioassays indicated that diethyl chlorophosphate or phosphite and diethyl chlorothiophosphite are specific for the sucker and stickleback.

EXAMPLE 12

(Exploratory assays with 1,2-dichloroethyl diethyl phosphate).

Bridgelip sucker and steelhead trout were treated with various concentrations of 1,2-dichloroethyl diethyl phosphate for 96 hours at 15 C. to determine approximate selectivity and safety indices.

In a 24-hour assay at 10 C. using artesian well water, almost 100% mortality of sucker was achieved at 0.3 mg/l of 1,2-dichloroethyl diethyl phosphate; almost no mortality occurred in trout at concentrations below 3.0 mg/l. The 24-hour selectivity index for trout versus sucker was 35 and the 24-hour safety index was 10. These bioassays substantiated preliminary findings that 1,2-dichloroethyl phosphate is selectively lethal to the suckers at concentrations nonlethal to trout.

EXAMPLE 13

(O,O-diethyl S-(2,2-dichlorovinyl thiophosphate)

Bridgelip sucker and steelhead trout were treated with various concentrations of 1,2-dichloroethyl diethyl phosphate and O,O-diethyl S-(2,2-dichlorovinyl) thiophosphate for 24 hours at 16 C. to compare the potency and selectivity of the two chemicals.

In 24-hour assays at 16 C. using artesian well water, a 100% mortality of sucker was achieved at a concentration of 0.1 mg/l of 1,2-dichloroethyl diethyl phosphate and at a concentration of 0.1 mg/l of O,O-diethyl S-(2,2-dichlorovinyl) thiophosphate; no mortality occurred in steelhead below 5.0 mg/l of the phosphate and below 1.0 mg/l of the thiophosphate. The bioassays show that the activity and selectivity of the two chemicals are very similar.

EXAMPLE 14

(2,2,1-trichlorovinyl diethyl phosphate and 2,2-dichloro-1-diethyl phosphonovinyl diethyl phosphate)

A series of exploratory bioassays was made with threespine stickleback and chinook exposed to selected concentrations of 2,2,1-trichlorovinyl diethyl phosphate in artesian well water at 10 C. The resulting data indicate that the trichloro-compound is almost as toxic to stickleback as 2,2,2,1-tetrachloroethyl diethyl phosphate. The trichloro-$LC_{100}$ for stickleback is essentially 11 µg/l and the $LC_0$ for chinook is about 16 µg/l. These values yield a 96-hour safety index of about 1.5, a much lower value than the 96-hour safety indices determined for the dichloro- and tetrachloro-derivatives. With minor exceptions stickleback and chinook suffered no mortalities after the first 24-hour exposure to the trichloro-derivative. Consequently, the selectivity and safety indices remained the same for the 8-day bioassay.

A series of exploratory bioassays were made with threespine stickleback and chinook exposed to selected concentrations of 2,2-dichloro-1-diethyl phosphonovinyl diethyl phosphate. The toxicity of both the phosphone and trichloro-compounds to stickleback were identical, the $LC_{50}$'s of both compounds being 8 µg/l. Apparently, the replacement of a chlorine atom in the 1-position of the vinyl carbon group of the trichloro-compound by the diethyl phosphonate radical has no affect on the activity of the resulting chemical (2,2-dichloro-1 diethyl phosphonovinyl diethyl phosphate) to stickleback.

Similarly, the $LC_{50}$'s for chinook with both chemicals were about the same (18 to 20 µg/l). However, the variance in percentage mortalities was slightly greater for the phosphone than for the trichloro-compound. Thus, the larger variance of the phosphone compound yielded the less desirable safety index of 0.9 as compared to the 1.5 of the trichloro-compound.

General Discussion

The optimum range of concentration of the dichloro- and tetrachloro-compounds varies with temperature, water quality, and species of compared fish. From the foregoing tables it can be seen that at any temperature from 5 to 15 C. there is a range of concentrations in which the toxicant will achieve a 100% mortality of stickleback without any harmful effects on salmon or trout. It is preferable that a concentration within this range be chosen. However, conditions may warrant using more or less than the preferred amount.

For field applications the concentration of the dichloro- and tetrachloro-compounds would vary with water quality—mainly with regard to water temperature and hydrogen ion concentrations. Generally, treated areas would contain water low in dissolved solids and a pH of 7 to 7.5. The activity of the chemicals would then be essentially similar to that determined in our tests using river water. For the treatment of rivers and shorelines of lakes the concentrations of the dichloro- and tetrachloro-compounds that would be used would be those that would kill stickleback or suckers in 12 to 24 hours. The information above, relating to Examples 1 and 12, substantiates improvement in fish culture by the addition of dichloroethyl or dichlorovinyl diethyl phosphate to an aqueous habitat at a concentration in water ranging between 0.1 and 10 mg/l. From our tests to date using natural river water, we can recommend 1.0 mg/l of 2,2-dichlorovinyl diethyl phosphate for control of suckers at 10 to 15 C. and 5 mg/l for control of stickleback at 10 C. and 3 mg/l at 15 C. to be safe and effective concentrations to apply at such locations where dilution makes the chemical harmless. The information above, relating to Example 2, substantiates improvement in fish culture by the addition of tetrachloroethyl diethyl phosphate to an aqueous habitat at a concentration in water ranging between 4 and 80 $\mu$g/l. We can recommend 20 $\mu$g/l of 2,2,2,1-tetrachloroethyl diethyl phosphate to be a safe and effective concentration to apply for control of suckers or stickleback at 10 or 15 C. at such locations where dilution makes the chemical harmless.

According to our data using river water suckers can be controlled in 24-hour applications or less with 2,2-dichlorovinyl diethyl phosphate at concentrations between 0.5 and greater than 10 mg/l for chinook at 10 C.
between 0.3 and greater than 5 mg/l for chinook at 15 C.
between 0.5 and greater than 6 mg/l for sockeye at 10 C.
between 0.5 and greater than 4 mg/l for Kamloops at 10 C.
between 0.3 and greater than 3 mg/l for Kamloops at 15 C.
between 0.5 and greater than 4.5 mg/l for cutthroat at 10 C.
between 0.3 and greater than 6 mg/l for cutthroat at 15 C.
between 0.3 and greater than 6 mg/l for brook trout at 15 C.

According to our data using river water stickleback can be controlled in 24-hour applications or less with 2,2-dichlorovinyl diethyl phosphate at concentrations between 4 and greater than 10 mg/l for chinook at 10 C.
between 2 and greater than 5 mg/l for chinook at 15 C.
between 4 and greater than 6 mg/l for sockeye at 10 C.
between 4 and greater than 4 mg/l for Kamloops at 10 C.
between 2 and greater than 3 mg/l for Kamloops at 15 C.
between 4 and greater than 4.5 mg/l for cutthroat at 10 C.
between 2 and greater than 6 mg/l for cutthroat at 15 C.
between 2 and greater than 6 mg/l for brook trout at 15 C.

According to our data using river water, suckers can be controlled in 24-hour applications or less with 2,2,2,1-tetrachloroethyl diethyl phosphate at concentrations between 10 and greater than 30 $\mu$g/l for chinook at 10 C.
between 10 and greater than 30 $\mu$g/l for coho at 10 C.
between 20 and greater than 80 $\mu$g/l for sockeye at 7.5 C.
between 10 and 40 $\mu$g/l for sockeye at 10 C.
between 10 and 50 $\mu$g/l for kokanee at 15 C.
between 10 and 30 $\mu$g/l for brook trout at 15 C.
between 10 and greater than 30 $\mu$g/l for cutthroat at 15 C.
between 10 and greater than 24 $\mu$g/l for Kamloops at 10 and 15 C.

According to our data using river water, stickleback can be controlled in 24-hour applications or less with 2,2,2,1-tetrachloroethyl diethyl phosphate at concentrations between 16 and greater than 30 $\mu$g/l for chinook at 10 C.
between 16 and greater than 30 $\mu$g/l for coho at 10 C.
between 20 and greater than 80 $\mu$g/l for sockeye at 7.5 C.
between 16 and 40 $\mu$g/l for sockeye at 10 C.
between 13 and 50 $\mu$g/l for kokanee at 15 C.,
between 13 and 30 $\mu$g/l for brook trout at 15 C.
between 13 and greater than 30 $\mu$g/l for cutthroat at 15 C.
between 13 and greater than 24 $\mu$g/l for Kamloops at 10 and 15 C.

According to our data using river water, stickleback can be controlled in 24-hour applications or less with 2,2-dichlorovinyl diethyl phosphate (2 Cl) and 2,2,2,1-tetrachloroethyl diethyl phospate (4 Cl) applied together at concentrations between 1350 $\mu$g/l of 2 Cl with 4.5 $\mu$g/l of 4 Cl and greater than 3000 $\mu$g/l of 2 Cl with 9 $\mu$g/l of 4 Cl for sockeye at 10 C.
between 1350 $\mu$g/l with 4.5 $\mu$g/l of 4 Cl and greater than 2400 $\mu$g/l of 2 Cl with 8 $\mu$g/l of 4 Cl for Kamloops at 10 C.

The results of exploratory bioassays with carp and catfish show that 2,2-dichlorovinyl diethyl phosphate is practical for treatment of rivers and shorelines of lakes.

According to our data using river water carp and bullhead catfish can be controlled in 24 to 30-hour applications or less with 2,2-dichlorovinyl diethyl phosphate at concentrations between 1 mg/l and greater than 10 mg/l for chinook at 10 C.
between 1 mg/l and greater than 6 mg/l for sockeye at 10 C.
between 1 mg/l and greater than 4 mg/l for Kamloops at 10 C.
between 1 mg/l and greater than 4.5 mg/l for cutthroat at 10 C.

The selective properties of the dichloro-compounds are so outstanding that suckers can be eradicated from ponds or lakes without harm to salmonids. Our tests have demonstrated that 100% mortality of the sucker can be achieved at distribution concentrations of 100 to 300 $\mu$g/l of 2,2-dichlorovinyl diethyl phosphate at 10 C. At 300 $\mu$g/l essentially no mortality of chinook or coho salmon occurred in 64-day bioassays at 10 C.

The information above, relating to Examples 3–6, substantiates improvement in fish culture by the addition of a mixture comprising 1 part tetrachloroethyl diethyl phosphate and 300 parts of dichloroethyl or dichlorovinyl diethyl phosphate. The concentration of dichloroethyl or dichlorovinyl diethyl phosphate ranges between 1.35 and 3 mg/l and the concentration of tetrachloroethyl diethyl phosphate ranges beteen 4.5 and 9 $\mu$g/l when applied in combination.

Due to the synergistic nature of the dichloro- and tetrachloro-compounds a 100% mortality of the sucker can be achieved in less than 96 hours at concentrations of 60 $\mu$g/l of the dichloro-compound by the addition of about one part of 2,2,2,1-tetrachloroethyl diethyl phosphate to 300 parts of 2,3-dichlorovinyl diethyl phosphate.

The selective properties of the tetrachloro-compounds are sufficiently outstanding that stickleback and sucker can be eradicated from ponds and lakes without harm to salmonids. Our tests have demonstrated that essentially 100% mortality of stickleback can be achieved at distributed concentrations of 6 to 4 µg/l of 2,2,2,1-tetrachloroethyl diethyl phosphate between 8 and 16 days at 10 C. and that the estimated $LC_{100}$ of the sucker would be essentially the same. Essentially no mortality of chinook or coho salmon occurred in 64-day bioassays at 10 C. when exposed to 6 µg/l or less of the chemical.

A gas chromatograph analysis of 2,2-dichlorovinyl diethyl phosphate in river water indicated that the compound has a half-life of less than 20 days at 15 C. A gas chromatograph analysis of 2,2,2,1-tetrachloroethyl diethyl phosphate in river water indicated that the compound has a half-life of about 11 days at 15 C. These analyses suggest why long exposures to low concentrations of the compounds are harmless to salmonids.

The presence of bacteria and other microorganisms affect the rate of degradation of the dichloro- and tetrachloro-compounds. Because of this the chemicals break down much faster in river water than in artesian well water or distilled water. For short term bioassays the potencies of the chemicals were not affected by the chemistry of the water. For example, our results showed that a concentration of 100 µg/l of the dichloro-compound was the 96-hour $LC_{100}$ for the bridgelip sucker in both artesian well water and river water at 10 C. Likewise, a concentration of 7 µg/l of the tetrachloro-compound was the 96-hour $LC_{100}$ for the threespine stickleback in both artesial well water and river water at 10 C.

The presence of a layer of river mud on the bottoms of glass aquaria that contained the river water decreased the half-life of the dichloro-compound from 43 days to 15 days at 15 C. The rate of deactivation was measured by bioassay with stickleback and the data were analyzed by conventional methods.

Some breakdown products of dichloro- and tetrachloro-compounds appear to be toxic and have a longer half-life. Breakdown products of these chemicals applied at recommended effective concentrations, however, are not lethal to salmonids as indicated by the results of our long-term static bioassays.

In combating the stickleback, sucker, bullhead and carp in accordance with this invention, it is desirable that the chemicals be added to a stream so that concentrations will be substantially uniform throughout the water system. Thus, the natural flow and movement of the water and/or the method of application might serve to facilitate the dispersion and mixing and reduce the amount of labor and equipment necessary for securing and maintaining the desired conditions.

The amount of chemical required did not depend to any appreciable extent upon the size or weight of the fish treated but appears to be equally lethal to stickleback, suckers, bullhead and carp of all sizes.

Because degradation tests with a mud substrate enhanced the survival of fish we assume that suspended organic materials or detritus on the bottom of aerated waters would contribute to the degradation of low concentrations of chemical appropriate to kill stickleback or sucker.

In treating a stream, pond or lake, chlorinated derivatives of diethyl phosphate may be added in liquid form as solutions, suspensions or emulsions. In general, aqueous solutions or dispersals are preferred because the application and mixing are more readily effected. The chemicals may be dissolved in water miscible solvents or it may be added in the form of a concentrated aqueous suspension. The chemical suspension may be prepared from a solution of nonpolar solvents, or the like, as necessary to alter the density of the solution to facilitate dispersion and mixing.

Depending on the species of desirable fish, and the temperature and chemistry of the water, optimum concentrations of chemical that flush out or dilute within an appropriate time period may be used in any waters. Bodies of water that fit these requirements include streams, estuaries, tidal pools and the shorelines of lakes and the coastal areas of the ocean.

The use of a deactivator could greatly increase the size of the selectivity and safety indices of chlorinated derivatives of diethyl phosphate.

The dichloro- and tetrachloro-derivatives of diethyl phosphate have been used extensively in the foregoing examples to demonstrate the extent that these compounds are specific for the sucker and stickleback. Cursory tests were made with seven other halogenated derivatives of diethyl phosphate to show the universal selectiveness of the group for the sucker and stickleback.

Bioassays with diethyl chlorophosphate and diethyl chlorophosphite demonstrate that the specificity of these organophosphates is not lost for these fishes when phosphite replaces phosphate. Theoretically the phosphite would change to phosphate when added to water that contains oxygen. Halogenated diethyl phosphites are therefore specific for the sucker and stickleback.

Bioassays made with O,O-diethyl S-(2,2-dichlorovinyl) thiophosphate and diethyl chlorothiophosphite demonstrate that the specificity of these organophosphates is not lost for suckers and stickleback when sulphur replaces oxygen to change the compound from a phosphate to a thiophosphate. Theoretically, the thiophosphate should be more active than the phosphate compound—a condition which was slightly evident in our test results. Thus, we claim that chlorinated diethyl thiophosphates are specific for the sucker and stickleback.

The potency or biological activity of the diethyl phosphates varies with the number of chlorine atoms. Diethyl chlorophosphate or phosphites which contains a single chlorine atom are less potent than multichlorinated compounds. The 1,2-dichloroethyl diethyl and 2,2-dichlorovinyl diethyl phosphate and the O,O-diethyl S (2,2-dichlorovinyl) thiophosphate are about equally active, whereas the 2,2,1-trichlorovinyl diethyl phosphate and the 2,2,2,1-tetrachloroethyl diethyl phosphate are about 100 times more active than the dichloro-compounds with the same species of fish: the trichloro- being slightly less active than the tetrachloro-compound.

Previously published exploratory assays with O,O-dimethyl O-(2,2-dichlorovinyl) phosphate (DDVP) showed no selectivity for stickleback or suckers although the chemical has been used to selectively eradicate undesirable animals from ponds without injuring carp. The fundamental difference between DDVP and the above-described chemicals selective for sucker and stickleback is the presence of two methyl groups (dimethyl) instead of two ethyl groups (diethyl) on the phosphate.

Theoretically, 2,2-dichlorovinyl diethyl phosphate hydrolyses to a vinyl alcohol and then undergoes molecular rearrangement through a series of relatively unstable compounds to form dichloroacetic acid. Bioassays with 10 chinook exposed to 100 mg/l of dichloroacetic acid for 192 hours at 10 C. showed that the salmon were not stressed and suffered no mortalities.

A method for detecting carcinogens and mutagens with Salmonella, a bacterium, was used to test the potential of 2,2-dichlorovinyl diethyl phosphate and 2,2,2,1-tetrachloroethyl diethyl phosphate for carcinogenic properties. Within the framework of a standard plate test samples of dichloro- and tetrachloro-compounds showed no mutagenic activity at concentrations of 0.5, 5, 50, 500, and 5000 mg/l when tested with five strains of Salmonella. In support of these findings we note that the very closely related compound, DDVP, has wide-spread use as an insecticide for agricultural and household purposes. It has also been used by veterinarians to eliminate gastrointestinal worms in swine, ruminants and horses. Considerable literature has been published on DDVP but none suggest that DDVP is a carcinogen or concentrates residues.

Having described our invention we claim:

1. A method of improving fish culture by control of the stickleback, sucker, carp or bullhead catfish populations in an aqueous habitat comprising sticklebacks, suckers, carp or bullhead catfish and at least one member selected from a group of desirable fishes comprising chinook salmon, coho salmon, sockeye salmon, kokanee, steelhead, Kamloops trout, cutthroat trout, brook trout and Arctic grayling, said method comprising:

adding to the aqueous habitat a compound containing diethyl esters of phosphoric, phosphorous, thiophosphoric or thiophosphorous acid that further contains a chloride or a chlorinated ethyl or vinyl group, the compound being added at an effective concentration operatively lethal to the stickleback, sucker, carp or bullhead catfish populations, but not operatively lethal to said selected members of the group of desirable fishes.

2. A method of fish culture as set out in claim 1, wherein the added compound is dichloroethyl or dichlorovinyl diethyl phosphate at a concentration in water ranging between 0.1 and 10 mg/l.

3. A method of fish culture as set out in claim 1 wherein the added compound is tetrachloroethyl diethyl phosphate at a concentration in water ranging between 4 and 80 $\mu$g/l.

4. A method of fish culture as set out in claim 1 wherein the added compound is in the form of a mixture comprising 1 part tetrachloroethyl diethyl phosphate and 300 parts of dichloroethyl or dichlorovinyl diethyl phosphate.

5. A method of fish culture as set out in claim 4 wherein the concentration of dichloroethyl or dichlorovinyl diethyl phosphate ranges between 1.35 and 3 mg/l and the concentration of tetrachloroethyl diethyl phosphate ranges between 4.5 and 9 $\mu$g/l when applied in combination.

6. A method of fish culture as set out in claim 2 further comprising the step of subsequently treating the aqueous habitat with activated carbon or potassium permanganate to decrease the toxic effects of the dichloroethyl or dichlorovinyl diethyl phosphate.

* * * * *